US011507336B2

United States Patent
Blume et al.

(10) Patent No.: US 11,507,336 B2
(45) Date of Patent: Nov. 22, 2022

(54) AUGMENTED REALITY DISPLAY SHARING

(71) Applicant: SentiAR, Inc., St. Louis, MO (US)

(72) Inventors: Walter Blume, Edwardsville, IL (US); Michael K. Southworth, St. Louis, MO (US)

(*) Notice: Subject to any disclaimer, the term of this patent is extended or adjusted under 35 U.S.C. 154(b) by 0 days.

(21) Appl. No.: 17/224,943

(22) Filed: Apr. 7, 2021

(65) Prior Publication Data
US 2021/0224020 A1    Jul. 22, 2021

Related U.S. Application Data

(63) Continuation of application No. 16/275,104, filed on Feb. 13, 2019, now Pat. No. 11,003,410.
(Continued)

(51) Int. Cl.
  *G06F 3/14* (2006.01)
  *G06F 3/01* (2006.01)
  (Continued)

(52) U.S. Cl.
  CPC ............ *G06F 3/1454* (2013.01); *G06F 3/013* (2013.01); *G06F 3/017* (2013.01); *G06F 3/147* (2013.01);
  (Continued)

(58) Field of Classification Search
  CPC ........ G06F 3/1454; G06F 3/013; G06F 3/017; G06F 3/147; G06F 1/163; G06F 3/011; G09G 5/005; G09G 2320/0261; G09G 2340/0492; G09G 2340/12; G09G 2354/00; G09G 2356/00; G09G 2370/042; G09G 2380/08; G10L 15/26; G16H 20/40; G16H 40/63; G16H 40/67
  See application file for complete search history.

(56) References Cited

U.S. PATENT DOCUMENTS 7,240,111 B2    7/2007  VanHarlingen et al.
7,567,233 B2    7/2009  Garibaldi et al.
(Continued)

OTHER PUBLICATIONS

Alcantarilla, P. et al., "Fast Explicit Diffusion for Accelerated Features in Nonlinear Scale Spaces," British Machine Vision Conference, Sep. 2013, 11 pages.
(Continued)

*Primary Examiner* — Mark W Regn
(74) *Attorney, Agent, or Firm* — Fenwick & West LLP

(57) ABSTRACT

A visualization system provides graphics for presentation on displays of multiple users who may be wearing head-mounted displays (HMDs). In an embodiment, the system determines that a first gaze direction of a first user is directed toward a first display. The system determines user inputs performed by the first user. The user inputs may be hands-free such as gestures of a hand or finger or voice commands. The system generates a graphical annotation using the user inputs. The system provides the graphical annotation to a first HMD for presentation to the first user. The system determines a second display paired to the first display. The system provides the graphical annotation to a second HMD for presentation to a second user looking at the second display. The displays may include a physical display or a virtual display, for example, in an augmented reality environment.

20 Claims, 6 Drawing Sheets

Related U.S. Application Data

(60) Provisional application No. 62/630,186, filed on Feb. 13, 2018.

(51) Int. Cl.
  *G09G 5/00* (2006.01)
  *G06F 3/147* (2006.01)
  *G10L 15/26* (2006.01)

(52) U.S. Cl.
  CPC ..... *G09G 5/005* (2013.01); *G09G 2320/0261* (2013.01); *G09G 2340/0492* (2013.01); *G09G 2340/12* (2013.01); *G09G 2354/00* (2013.01); *G09G 2356/00* (2013.01); *G09G 2370/042* (2013.01); *G09G 2380/08* (2013.01); *G10L 15/26* (2013.01)

(56) References Cited

U.S. PATENT DOCUMENTS

| | | | |
|---|---|---|---|
| 9,829,970 B2 | 11/2017 | Ellis et al. | |
| 11,003,410 B2* | 5/2021 | Blume | G06F 3/147 |
| 2003/0025849 A1* | 2/2003 | Hara | G02B 27/0172 |
| | | | 349/56 |
| 2010/0042763 A1 | 2/2010 | Bica | |
| 2010/0083122 A1 | 4/2010 | Kozloski et al. | |
| 2010/0232340 A1* | 9/2010 | Godor | H04N 21/234327 |
| | | | 370/312 |
| 2010/0302156 A1 | 12/2010 | Arthur | |
| 2010/0325322 A1 | 12/2010 | Crucs | |
| 2012/0182210 A1 | 7/2012 | Chan et al. | |
| 2013/0335303 A1* | 12/2013 | Maciocci | G06F 3/013 |
| | | | 345/8 |
| 2014/0094687 A1 | 4/2014 | Razzaque et al. | |
| 2016/0093108 A1 | 3/2016 | Mao et al. | |
| 2016/0147302 A1 | 5/2016 | Choi | |
| 2016/0203648 A1 | 7/2016 | Bilbrey et al. | |
| 2016/0283455 A1* | 9/2016 | Mardanbegi | G06F 3/038 |
| 2016/0301791 A1* | 10/2016 | Kim | G04G 21/04 |
| 2016/0353055 A1 | 12/2016 | Popescu et al. | |
| 2016/0379606 A1 | 12/2016 | Kollin et al. | |
| 2017/0366554 A1 | 12/2017 | Hook et al. | |
| 2018/0161676 A1 | 6/2018 | Ikeda et al. | |

OTHER PUBLICATIONS

PCT International Search Report and Written Opinion, PCT Application No. PCT/US19/17852, dated May 1, 2019, 17 pages.

United States Office Action, U.S. Appl. No. 16/275,104, dated Sep. 4, 2020, 24 pages.

United States Office Action, U.S. Appl. No. 16/275,104, dated Apr. 23, 2020, 19 pages.

\* cited by examiner

AUGMENTED REALITY DISPLAY SHARING

CROSS REFERENCE TO RELATED APPLICATIONS

This application is a continuation of co-pending U.S. application Ser. No. 16/275,104, filed Feb. 13, 2019, which claims the benefit of priority to U.S. Provisional Application No. 62/630,186, filed on Feb. 13, 2018, all of which are incorporated herein by reference in their entirety for all purposes.

TECHNICAL FIELD

This disclosure generally relates to a visualization system for an augmented reality environment.

BACKGROUND

In conventional medical interventional and surgical suites, there are often considerations where one or more operators work in a sterile surgical field while other support personnel are stationed in a separate non-sterile area. The coordinated use of multiple medical systems, each of which having their own display monitors, presents obstacles to efficient use. For example, information displayed on the monitors is often duplicated between two or more different physical locations.

In some use cases, an operating physician must maintain sterility within the sterile field. During critical periods of a procedure, the operating physician may need to maintain both hands on medical instruments, e.g., catheters, guidewires, etc. The requirement of sterility may limit the number and type of medical information systems with which the operating physician can interact. The sterility requirement may also limit the interactivity of the medical information systems by requiring sterile bagging procedures. The requirement of maintaining both hands on medical instruments during critical periods of the procedure may preclude or interfere with the ability of personnel to use conventional medical information system interfaces.

BRIEF DESCRIPTION OF THE FIGURES

The disclosed embodiments have advantages and features which will be more readily apparent from the detailed description, the appended claims, and the accompanying figures (or drawings). A brief introduction of the figures is below.

SUMMARY

A visualization system provides graphics for presentation on displays of multiple users who may be wearing head-mounted displays. In an embodiment, a method comprises receiving sensor data from a first head-mounted display (HMD) of a first user. The method further comprises determining, using the sensor data, that a first gaze direction of the first user is directed toward a first display. The method further comprises determining, using the sensor data, one or more user inputs performed by the first user. The method further comprises generating a graphical annotation using the one or more user inputs. The method further comprises providing the graphical annotation to the first HMD for presentation to the first user. The method further comprises determining a second display paired to the first display. The method further comprises providing the graphical annotation to a second HMD for presentation to a second user for allowing a second gaze direction of the second user to be directed toward the second display.

In an embodiment, a system comprises a first head-mounted device (HMD) of a first user and a second HMD of a second user. The system further comprises a non-transitory computer-readable storage medium storing instructions, the instructions when executed by one or more processors cause the one or more processors to perform steps including receiving sensor data from the first HMD. The steps further include determining, using the sensor data, that a first gaze direction of the first user is directed toward a first display. The steps further include determining, using the sensor data, one or more user inputs performed by the first user. The steps further include generating a graphical annotation using the one or more user inputs. The steps further include providing the graphical annotation to the first HMD for presentation to the first user. The steps further include determining a second display paired to the first display. The steps further include providing the graphical annotation to the second HMD for presentation to the second user for allowing a second gaze direction of the second user to be directed toward the second display.

DETAILED DESCRIPTION

I. Example System Overview

Figure 1:
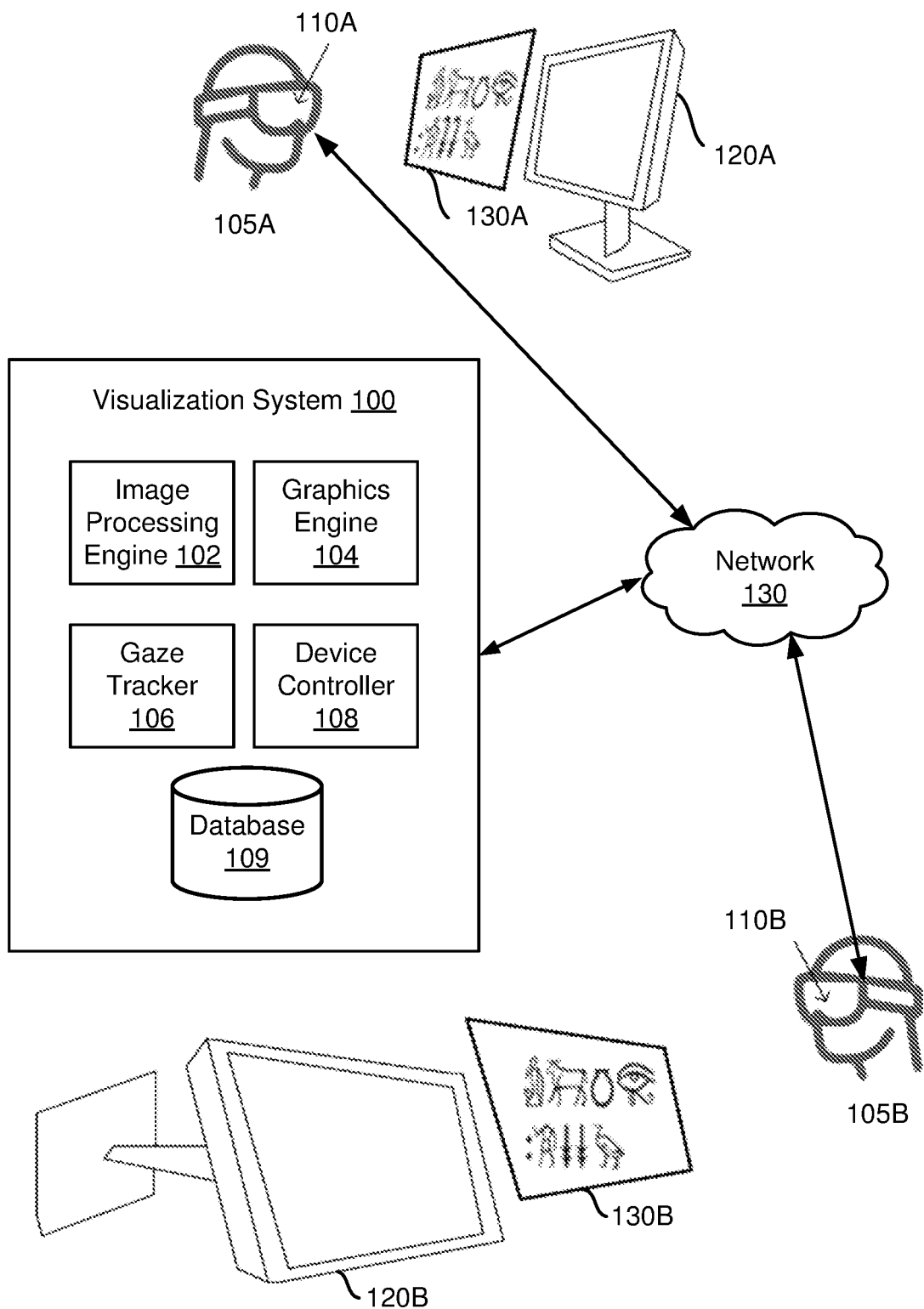
FIG. 1 is a diagram of a system environment for a visualization system according to an embodiment.

FIG. 1 illustrates an example system environment for a visualization system 100 according to an embodiment. The system environment shown in FIG. 1 includes the visualization system 100 and a number of head-mounted displays (HMDs) 110 of users 105, which are communicatively connected to each other via a network 130 (e.g., the Internet or wireless access point). The system environment also includes a number of displays 120. In other embodiments, different or additional entities can be included in the system environment. For example, although two HMDs 110A and 110B of users 105A and 105B, respectively, and two corresponding displays 120A and 120B, are shown in FIG. 1, in other embodiments, the system environment may include any other number of HMDs 110 of users 105 and/or displays 120. The functions performed by the various entities of FIG. 1 may vary in different embodiments.

In the embodiment shown in FIG. 1, a first user 105A wearing a first HMD 110A faces a first display 120A. A second user 105B wearing a second HMD 110B faces a second display 120B, which may be located at a different physical location (in the real world) than the first display 120A or first user 105A. A display 120 may be a physical display (e.g., computer monitor, laptop, phone, tablet, or another type of device) or a virtual display.

A virtual display may be a graphic generated by a HMD 110 (or visualization system 100) for display to a user wearing the HMD 110. For example, in an augmented, virtual, artificial, or mixed reality environment, a user may perceive the virtual display as a two-dimensional (2D) or three-dimensional (3D) floating-in-the-air graphic or hologram. A virtual display may be standalone, i.e., not necessarily associated with a physical display. The virtual display may be at least partly transparent. In some embodiments, the HMD 110 may display a virtual display overlaid on at least part of physical display. For example, the overlaid virtual display may be a control such as a user interface button. As another example, the overlaid virtual display may include any combination of text or graphics such as a chart, video, or photo.

Additionally, the HMD 110 may position a virtual display using position of a physical display, e.g., to display the virtual display nearby or in front of the physical display. The visualization system 100 may provide seamless mapping of a virtual display to a physical display to share information (e.g., annotations) between the displays. Displays 120 may vary in size, shape, display resolution, or other attributes. For example, the visualization system 100 may scale a graphic of one display for mapping to another display that is larger or smaller in size.

I. A. Head-Mounted Display

A head-mounted display (HMD) 110 may include one or more of: an electronic display, a camera, and a sensor to detect user input. The electronic display is configured to display images to a user in accordance with data received from the visualization system 100, another HMD 110, or another source. Moreover, the electronic display may display 3D imagery at positions in 3D space, e.g., in an augmented reality environment, virtual reality environment, or other types of artificial or mixed reality environments. A HMD 110 may generate a virtual model of a display and present the virtual model at an arbitrary position and scale in space. Examples of electronic displays include: a liquid crystal display (LCD), an organic light emitting diode (OLED) display, an active-matrix organic light-emitting diode display (AMOLED), a liquid crystal on silicon display (LCOS), some other display, or some combination thereof. In some embodiments, the electronic display may include one or more optical lens, optical waveguides, or optical combiners.

The camera may capture views of the real world as perceived by a user. For example, a camera in a front-facing position on the head of the user captures video or images of the field of view of the user. One or more processors of the visualization system 100 may analyze the image using computer vision techniques to recognize one or more displays present in the field of view of the user.

Sensors configured to detect user input may include a microphone to detect voice commands, motion sensors to detect hand gestures or gaze direction, among other types of sensors. The sensors may facilitate hands-free user inputs, for example, because voice commands, hand gestures, and changing gaze direction does not necessarily require a user to physically touch a user interface or control (e.g., a mouse or keyboard). This may be advantageous for use cases such as surgical procedures where a physician needs to maintain a sterile environment and/or may have both hands occupied, e.g., to handle a medical device. The HMD 110 may process sensor data using one or more onboard processors and provide detected user inputs to the visualization system 100.

The HMD 110 may also provide sensor data to the visualization system 100 for further processing or detection of user inputs.

Additionally, a HMD 110 may include one or more of: a sensor to capture information for determining position or orientation of the HMD 110 in physical space, a speaker for producing audio output, a wireless means to communicate information (e.g., display or sensor data) between HMDs or other types of devices, and one or more processors for computing or controlling the HMD 110. In some embodiments, one or more HMDs 110 may be a MICROSOFT HOLOLENS, though various other types of HMDs can also be used including HMDs custom-designed for a medical environment. Example sensors include accelerometers, gyroscopes, inertial measurement units (IMU), depth cameras, global positioning system (GPS) sensors, ultrasonic sensors, infrared sensors, and proximity sensors, among others.

In some embodiments, the visualization system 100 does not necessarily require a HMD 110. For example, the visualization system 100 may include an augmented reality device or another type of display device that is not worn on a head of user, e.g., a projector or display disposed on a wall or the ground.

I. B. Visualization System

The visualization system 100 includes an image processing engine 102, graphics engine 104, gaze tracker 106, device controller 108, and one or more databases 109. Alternative embodiments may include different or additional modules or omit one or more of the illustrated modules. The functions performed by the various modules may vary in different embodiments.

I. B. I. Image Processing

The image processing engine 102 detects displays by processing sensor data (e.g., video or images) captured by HMDs 110. The image processing engine 102 may use any number or types of computer vision techniques to automatically detect attributes of displays (e.g., physical or virtual). Attributes may include dimensions or edges of a display area of a display. In some embodiments, the image processing engine 102 may model the display area as a polygon such as a rectangle with a height and width. However, depending on the position and/or orientation of a viewing user and the display, the display area may be skewed (as illustrated in FIG. 1) rather than a rectangle. In other embodiments, the display area may be circular, elliptical, triangular, or have an arbitrary geometry.

Attributes may also include an orientation or position in space, e.g., relative to an environment such as a room. Additionally, attributes may include fiducial markings (e.g., a barcode or QR code) on the display or on another object in the surrounding environment, or specific content shown in the display.

The image processing engine 102 may determine that a display is present by comparing detected attributes to reference attributes stored in a database 109. The reference attributes may indicate known or pre-determined dimensions, orientation, or position of displays. The dimensions may be determined based on aspect ratios or sizes of a variety of displays, e.g., form factors ranging from computer monitors, tablets screens, or smartphone screens. Reference attributes may also include reference fiducial markings stored in the database 109. A reference fiducial marking may be associated with a specific display based on serial number or other identifying information.

In some embodiments, the image processing engine 102 may use an approximate position, orientation, dimensions, or content shown on displays as aids in identifying the function or position of the displays in physical or virtual space.

In some embodiments, the image processing engine 102 pairs two or more detected displays. The image processing engine 102 may pair displays responsive to determining that the displays have at least one attribute in common, e.g., size or dimension. Additionally, the image processing engine 102 may pair displays responsive to determining that users of the displays are participating in a same activity (e.g., surgery or medical procedure) or members of a same team. The image processing engine 102 may store information indicating pairings in the database 109.

In some embodiment, the image processing engine 102 may receive information indicating pairings, e.g., manually input by a user. In some embodiments, the image processing engine 102 automatically generates pairings by comparing content shown on displays, for example, using feature-based computer vision techniques (e.g., Speeded-Up Robust Features (SURF), Scale Invariant Feature Transform (SIFT), Oriented FAST and rotated BRIEF (ORB), etc.), descriptors or descriptor networks techniques, or statistical-based techniques (e.g., Random Sample Consensus (RANSAC) or mutual information, etc.), among other suitable techniques to identify matching displays.

In the embodiment shown in FIG. 1, the image processing engine 102 may determine that the first user 105A is facing the first display 120A by processing sensor data (e.g., video or images) captured by the first HMD 110A. Further, the image processing engine 102 may determine that the second user 105B is facing the second display 120B by processing sensor data captured by the second HMD 110B. The image processing engine 102 may pair the first display 120A and the second display 120B.

I. B. II. Graphics and Annotations

The graphics engine 104 provides graphics, e.g., virtual displays and annotations, or other information for presentation to users of the visualization system 100. The graphics engine 104 may provide graphics for presentation via any combination of one or more HMDs 110 or physical displays. The graphics engine 104 may also provide information indicating pairings for display to users. In some embodiments, responsive to determining that a physical display is not present or viewable by a user at a certain physical location, the graphics engine 104 provides a virtual display for presentation by a HMD 110 of the user. The graphics engine 104 may manage graphics of displays of multiple users, e.g., at different physical locations in the real world.

The graphics engine 104 generates annotations according to input by a user. Example annotations include text, labels, markers, selections (e.g., from a menu or list of options), drawings, sketches, or other types of information that may be shown on a display. The graphics engine 104 may generate an annotation responsive to detecting user inputs including hand or finger gestures, head movement, eye gaze movement, or voice commands. The visualization system 100 may use techniques for gesture detection or voice detection (e.g., speech-to-text algorithms) known to one skilled in the art.

In the embodiment shown in FIG. 1, the graphics engine 104 may generate the first annotation 130A responsive to input from the first user 105A. For instance, the first user 105A uses a hand or one or more fingers to draw a sketch while interacting with the first display 120A. Using information from the database 109, the graphics engine 104 may determine that the first display 120A is paired with the second display 120B. In response, the graphics engine 104 generates a second annotation 130B (matching at least in part or corresponding to the first annotation 130A) and provides the second annotation 130B to the second HMD 110B for display to the second user 105B. As shown in FIG. 1, the second annotation 130B may be presented as a virtual display overlaid on or in front of the second display 120B.

In some embodiments, the graphics engine 104 may determine that the dimensions or orientation of the first display 120A differs from that of the second display 120B. In response, the graphics engine 104 performs one or more transformations (e.g., scale or transpose) on the first annotation 130A to generate the second annotation 130B that fits the display area of the second display 120B. The first annotation 130A and the second annotation 130B may each include a same control shared by both users.

Sharing of annotations may be advantageous because users of the visualization system 100 may communicate or interact with each other using natural and intuitive user controls. In various embodiments, the user controls are hands-free, which allows users to operate in a sterile environment such as a procedure room for surgery or other medical interventions.

I. B. III. Gaze Tracking

The visualization system 100 may determine gaze direction of a user at a certain point in time using orientation of the head of the user, orientation of a pupil of the user, or some combination thereof. The gaze tracker 104 (or HMD 110) may determine an estimate of gaze direction of a user using orientation of the HMD 110 worn by the user, e.g., by processing sensor data of the HMD 110. The orientation may indicate a certain angle in one or more dimensions relative to one or more references axes of the room (e.g., 45 degrees leftwards and 10 degrees upwards).

I. B. IV. Device Controls

The device controller 108 maps user inputs to device controls. In some embodiments, the device controller 108 determines that a display (e.g., detected by the image processing engine 102) is associated with an input device such as a mouse, trackball, pen, joystick, or keyboard. In response, the device controller 108 maps user inputs (e.g., gaze direction, hand motions, or finger gestures) to device controls for a processor associated with the display. For example, the device controller 108 may map changes in gaze direction to mouse movements to control a cursor position on a display. As another example, the device controller 108 may map a hand motions to a (e.g., left or right) mouse click. Additionally, the device controller 108 may map finger gestures to selection of a certain key or button of a keyboard. Thus, the visualization system 100 may allow user interaction with a display without requiring the user to physically touch an input device.

II. Example Process Flow

Figure 2:
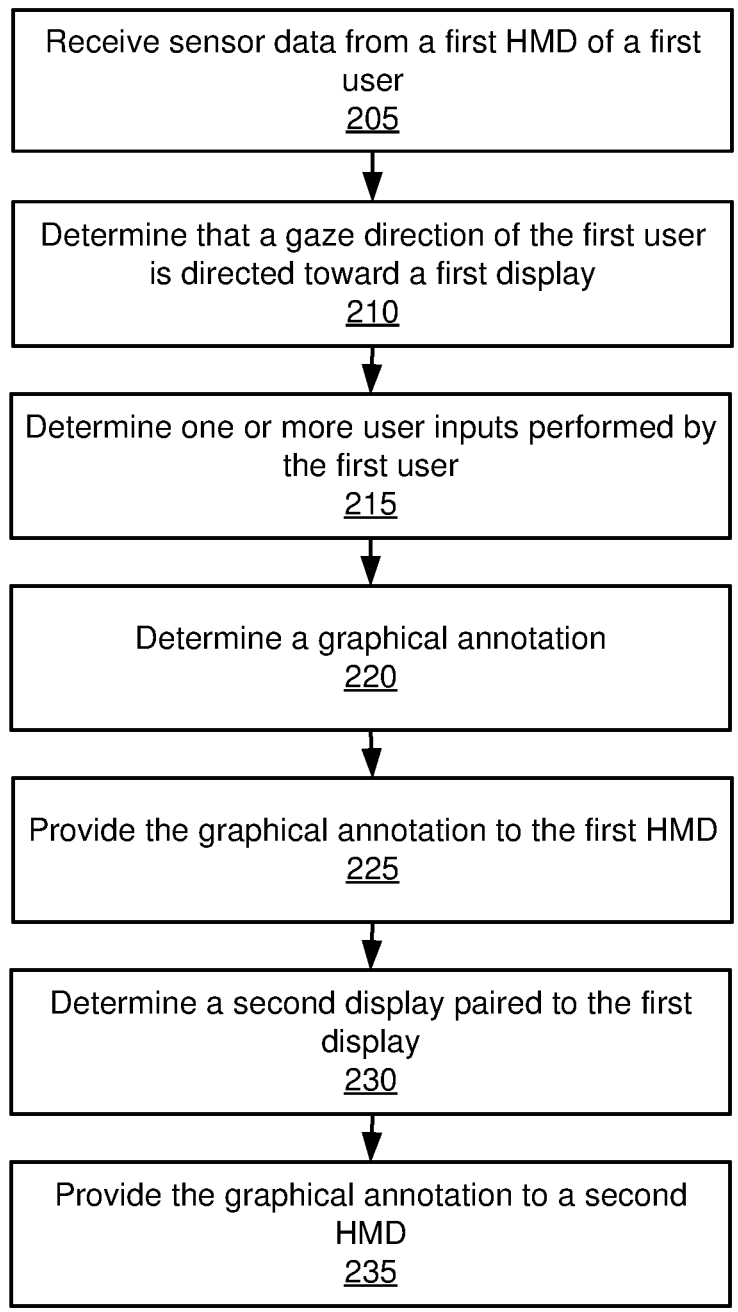
FIG. 2 is a flowchart of a process for providing a graphical annotation by the visualization system according to an embodiment.

FIG. 2 is a flowchart of a process 200 for providing a graphical annotation by the visualization system 100 according to an embodiment. The process 200 may include different or additional steps than those described in conjunction with FIG. 2 in some embodiments or perform steps in different orders than the order described in conjunction with FIG. 2.

The visualization system 100 receives 205 sensor data from a first HMD of a first user. The visualization system 100 determines 210 that a first gaze direction of the first user is directed toward a first display. The visualization system 100 may use the sensor data to determine the gaze direction. For example, the sensor data is captured by a motion sensor indicating motion, position, or orientation of the head or eyes of the first user.

In an embodiment, the visualization system 100 determines a field of view of the first user using the first gaze direction. Additionally, the visualization system 100 determines that the field of view includes the first display. The sensor data may include an image captured by a camera of the first HMD. In an embodiment, the visualization system 100 determines that the field of view includes the first display by detecting a fiducial marker in the image. Further, the visualization system 100 determines that the fiducial marker is associated with the first display. In a different embodiment, the visualization system 100 determines that the field of view includes the first display by determining one or more features in the image. Additionally, the visualization system 100 compares the one or more features with one or more reference features associated with the first display.

The visualization system 100 determines 215 one or more user inputs performed by the first user. The visualization system 100 may use the sensor data to determine the user inputs. As an example, the visualization system 100 determines that the one or more user inputs performed by the first user includes a voice command (e.g., based on sensor data from a microphone of the first HMD). Moreover, the visualization system 100 determines a transcript of the voice command. The visualization system 100 may generate the graphical annotation using the transcript.

As a different example, the visualization system 100 determines that the one or more user inputs performed by the first user includes a gaze direction or gesture of a hand or one or more fingers of the first user (e.g., based on sensor data from a motion sensor of the first HMD). In addition, the visualization system 100 maps the gaze direction or gesture to a device control associated with a physical input device. The visualization system 100 may generate the graphical annotation using the device control.

The visualization system 100 generates 220 a graphical annotation using the one or more user inputs. The visualization system 100 provides 225 the graphical annotation to the first HMD for presentation to the first user. In some embodiments, the first display is a physical monitor, and the first HMD presents the graphical annotation as a virtual display overlaid at least in part on the physical monitor.

The visualization system 100 determines 230 a second display paired to the first display. In some embodiments, the visualization system 100 determines that the first user is associated with the first display. The visualization system 100 determines that the second user is associated with the second display. The visualization system 100 may determine the pairing by determining that the first user and the second user are participating in a same activity. In other embodiments, the visualization system 100 may determine the pairing by determining that two or more displays are located in a same room or within a threshold distance from each other. In some embodiments, the visualization system 100 may determine the pairing based on pre-determined pairings or pairings manually input by a user.

The visualization system 100 provides 235 the graphical annotation to a second HMD for presentation to a second user. The visualization system 100 may provide the graphical annotation to the second HMD responsive to determining that a second gaze direction of the second user is directed toward the second display. In some embodiments, the second display is a virtual display generated by the second HMD, and the second HMD presents the graphical annotation by updating the virtual display. In some embodiments, responsive to determining that the first display has different dimensions than the second display, the visualization system 100 performs one or more transformations of the graphical annotation.

III. Example Display Detection Using Fiducial Marker

Figure 3A:
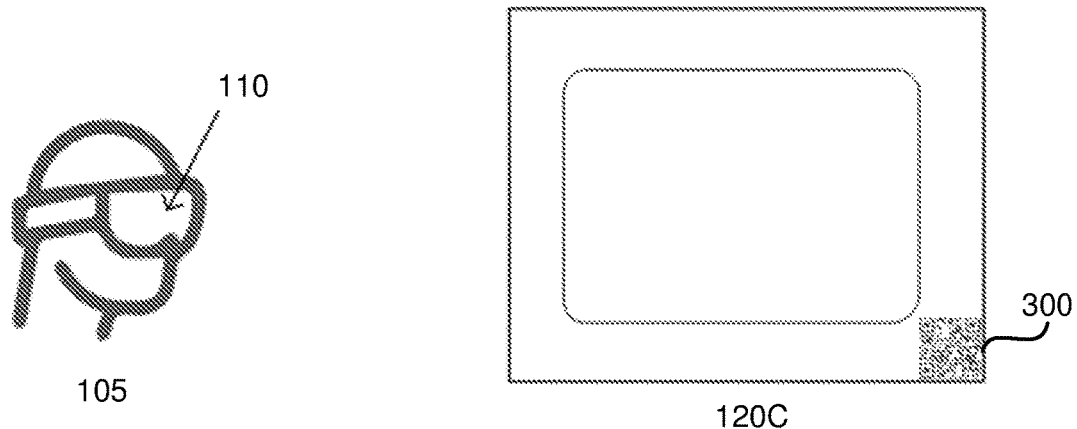
FIG. 3A is a diagram of a display including a fiducial marker according to an embodiment.

FIG. 3A is a diagram of a display including a fiducial marker according to an embodiment. The display 120C includes at least one fiducial marker 300. Example fiducial markers include a QR code (e.g., described by the ISO/IEC 18004 standard), a bar code, a graphic, or a reference point or measure, among other types of markers. The fiducial marker 300 may have a high contrast to facilitate detection by the image processing engine 102. The fiducial marker 300 may also have a known position relative to a display area of the display 120C. In the example shown in FIG. 3A, the fiducial marker 300 is positioned on the bottom right corner. In other embodiments, a fiducial marker may be located at a different position. The image processing engine 102 may process an image (or video) captured by the HMD 110 of a user 105, where the image includes the fiducial marker 300. Responsive to detecting the fiducial marker 300 in the image, the image processing engine 102 may determine a 3D planar orientation of the corresponding display 120C, e.g., relative to reference coordinate planes based on X, Y, and Z axis.

Figure 3B:
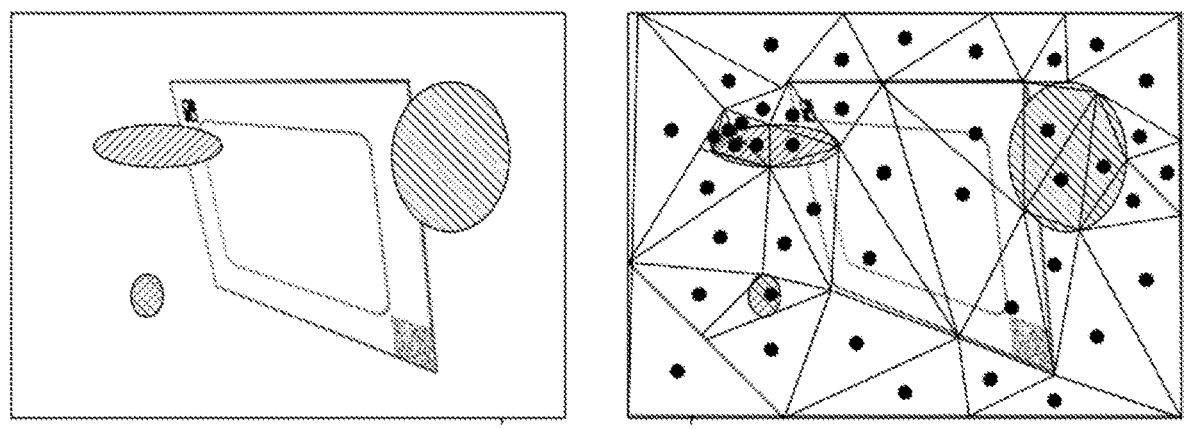
FIG. 3B is a diagram of an image of a display before and after processing according to an embodiment.

FIG. 3B is a diagram of an image of a display before and after processing according to an embodiment. In an embodiment, the visualization system 100 receives an image of a display including a fiducial marker. As shown in FIG. 3A, the image may be captured by a HMD 110 of a user 105. The image processing engine 102 may estimate distance and pose of the HMD 110 relative to the display using position and/or orientation surface information of the imaged display. As illustrated by the shaded ellipses in FIG. 3B, the image may include visual clutter at least partially obscuring the display. Visual clutter may be due to, for example, obstacles or contamination of a camera lens. The image processing engine 102 may represent the position and/or orientation surface information using a set of triangle vertices and depth information at centers of the triangles. As illustrated by the dots in FIG. 3B, centers of the triangles each represent an average distance between the HMD 110 (e.g., having the camera that captured the image) to the respective triangular area. In other embodiments, the image processing engine 102 may model position and/or orientation surface information using other types of geometry. The image processing engine 102 may use distances and/or orientations of the triangles to filter visual clutter or improve fitting of the computed representation of the display position. In particular, the image processing engine 102 may compare fit of an imaged display to an expected size or shape of a plane (e.g., displayable area) of the display.

In some embodiments, the image processing engine 102 uses the position and/or orientation surface information to detect a fiducial marker. In particular, the image processing engine 102 may use the position and/or orientation surface information to focus a search space within an image to scan for one or more fiducial markers. The focused search may be advantageous because the image processing engine 102 may reduce the compute power or other computational resources required to detect fiducial markers in captured images. To detect a fiducial marker, the image processing engine 102 may use a detection algorithm including one or more computer vision techniques known to one skilled in the art.

In some embodiments, the image processing engine 102 uses a detected position (e.g., origin location) and/or orientation of a fiducial marker to refine an estimate of the position and/or orientation of the display having the fiducial marker. Using the refined estimate, the image processing engine 102 may determine a 3D coordinate transform. The image processing engine 102 may use the 3D coordinate transform to modify graphics or virtual displays provided to a HMD 110 for presentation. The image processing engine 102 may provide the 3D coordinate transform a HMD 110 for rendering graphics for presentation to a user, for example, annotations overlaid on a display.

IV. Example Display Detection Using Feature Matching

Figure 4:
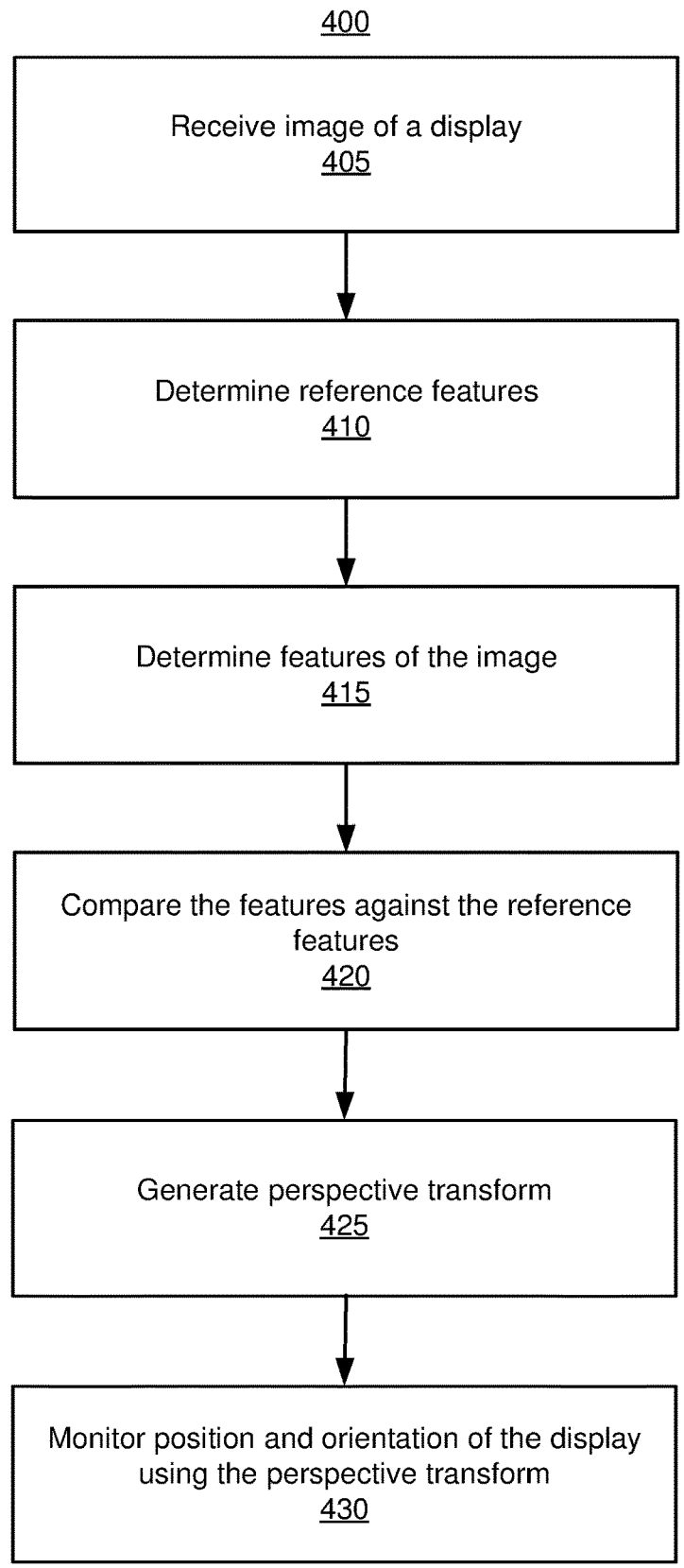
FIG. 4 is a flowchart of a process for detecting a display according to an embodiment.

FIG. 4 is a flowchart of a process 400 for detecting a display according to an embodiment. The image processing engine 102 may determine location of a display using the process 400 without necessarily requiring a fiducial marker. The image processing engine 102 receives 405 an image of a display. The image may be captured by a camera of a HMD 110 worn by a user 105, e.g., facing toward the display.

The image processing engine 102 determines 410 reference features by processing a template image of a reference display using an image classifier. The image processing engine 102 may access the database 109 to retrieve the template image, which indicates real-world dimensions of the reference display. The reference features may include a set of key points or descriptors of the reference display. An example algorithm for the image classifier when reference imagery is available is using the AKAZE feature detector described in "Fast Explicit Diffusion for Accelerated Features in Nonlinear Scale Spaces" by Pablo F. Alcantarilla, Jesús Nuevo, and Adrien Bartoli, published in the British Machine Vision Conference (BMVC), Bristol, UK, September 2013. Other example image classifier algorithms include neural nets or tensor graphs.

The image processing engine 102 generates 415 features of the image by applying the feature detector on the image. The features may include a set of key points or descriptors of the display. The image processing engine 102 compares 420 the features against the reference features. In particular, the image processing engine 102 may use a matching algorithm to determine levels of similarity between key points or descriptors of the display and the reference display. Responsive to determining that a level of similar satisfies a threshold criterion, the image processing engine 102 may match the corresponding features.

In some embodiments, the image processing engine 102 uses a Hamming distance for the matching algorithm. The image processing engine 102 determines the Hamming distance between features to find pairs of key points with a minimum Hamming distance between their descriptors. The image processing engine 102 may iterate through each key point to find these matching pairs of key points. The image processing engine 102 may sort the matched pairs by the Hamming distance. In some embodiments, the image processing engine 102 uses matching pairs of key points with a Hamming distance lower than a threshold value to filter unlikely matches (e.g., outliers or artifacts in the data).

The image processing engine 102 generates 425 a perspective transform by applying a fitting algorithm (e.g., least squares fit) to the matching pairs. The perspective transform describes the 3D location and orientation of the display within the capture image, i.e., from the perspective of a user wearing the HMD 110.

The image processing engine 102 monitors 430 position and orientation of the display using the perspective transform. The image processing engine 102 may use one or more linear feature detectors, corner detectors, or template matching techniques to extract a display region from the image for monitoring. Using the image data detected during the monitoring, the image processing engine 102 may determine an estimate distance from a point of the HMD 110 (e.g., camera capturing the images) to a point of a surface an object, e.g., in a same room as the user 105 wearing the HMD 110. The image processing engine 102 may use the estimate distance to determine an expected size of a display within a captured image, e.g., for image template matching operations.

V. Example Gaze Tracking

Figure 5:
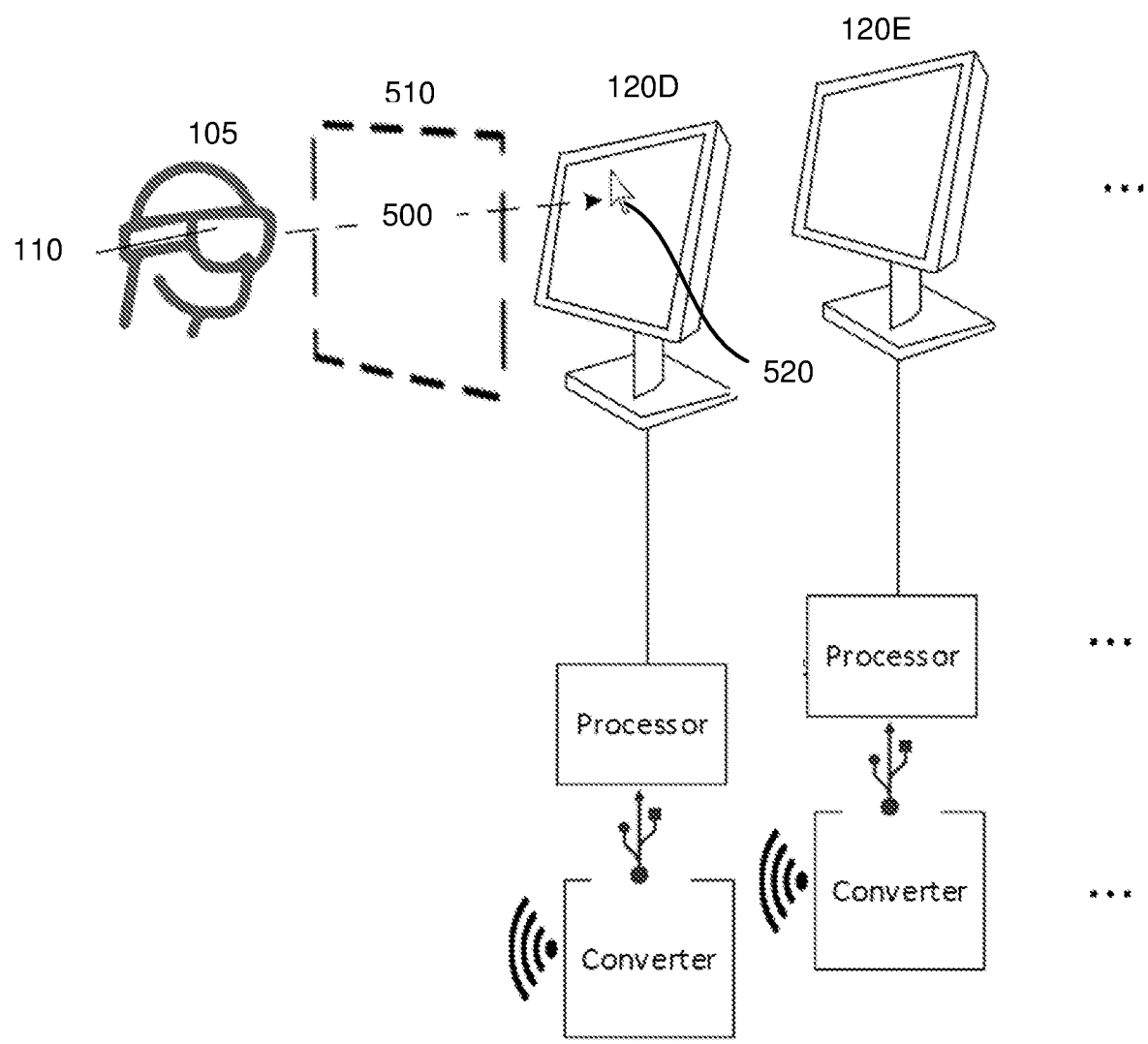
FIG. 5 is a diagram of tracking gaze direction according to an embodiment.

FIG. 5 is a diagram of tracking gaze direction according to an embodiment. The visualization system 100 provides manipulation of input devices such as a mouse for controlling a cursor on one or more displays. The visualization system 100 may use known pose and position of one or more displays to provide manipulation of an input device. In the embodiment shown in FIG. 5, a first display 120D and a second display 120E may have different pose and/or position.

Additionally, the visualization system 100 may provide the manipulation of the input device using gaze direction 500 or gestures of a user 105 wearing an HMD 110. The gaze tracker 106 may use a smoothing algorithm to smooth or filter sensor data to determine a gaze direction 500. For example, the smoothing algorithm may remove tremor in the sensor data indicative of the gaze direction 500, e.g., motion of the head or eyes of the user 105.

In an embodiment, the gaze tracker 106 performs smoothing algorithm using a running average combined with a standard deviation of the running average to recognize when the gaze direction 500 is dwelling on a display (or another object) or moving, e.g., without a focus. In an embodiment, responsive to determining that the standard deviation is less than a lower threshold, the gaze tracker 106 smooths the sensor data using the running average of the gaze ray. In an embodiment, responsive to determining that the standard deviation of the running average is greater than an upper threshold, the gaze tracker 106 determines that the gaze is moving rapidly and thus does not perform smoothing, or performs less smoothing.

The gaze tracker 106 may project in 2D or 3D space a ray formed by the gaze direction 500 outward from the HMD 110. Responsive to determining that the ray intersects with a plane of a known display, the gaze tracker 106 determines that the user 105 is looking at the display (e.g., a field of view of the user is directed toward the display) and thus selects the display. Responsive to determining that the ray intersects with planes of more than one known display, the gaze tracker 106 may select the display closest in proximity to the user 105 and HMD 110. In the example shown in FIG. 5, the gaze tracker 106 may select the display 120D.

The visualization system 100 may provide device controls to the selected display 120D or update graphics for presentation by the display 120D or for presentation by the HMD 110 in a virtual display 510 overlaid on the display. The graphics engine 104 may generate the virtual display 510 to indicate the selected display to the user 105. The virtual display 510 may include an annotation or another type of graphic.

In some embodiments, the device controller 108 (or HMD 110) converts position of the gaze direction 500 to a 2D mouse position. Additionally, the device controller 108 may convert user gestures to mouse state information (e.g., motion in up, down, left, right, in another direction). The device controller 108 may transmit the mouse position or mouse state information via a wireless transmitter of the HMD 110 (or wirelessly from the visualization system 100) to a receiver communicatively coupled to a processor of the display 120D. A converter may convert the received information and provide the converted information via a Universal Serial Bus (USB) protocol to the processor. The processor maps the converted information to a cursor position 520 for presentation of the display 120D. The processor may use smoothing techniques on the cursor position 520.

In another embodiment, responsive to determining that the user 105 is looking at display 120E, the visualization system 100 may provide device controls to selected display 120E or update graphics for presentation by the display 120E or for presentation by the HMD 110 in a virtual display overlaid on the display 120E.

VI. Example Interaction with Virtual Display

Figure 6:
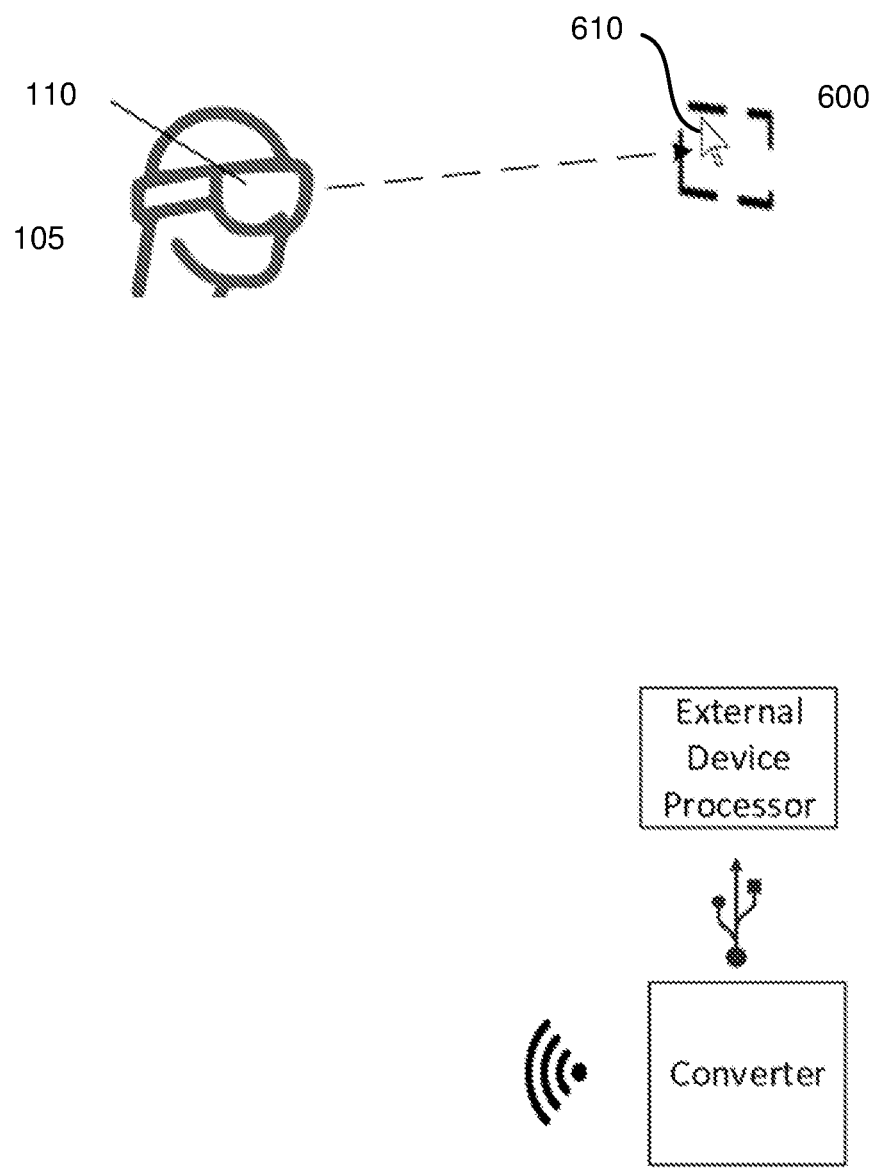
FIG. 6 is a diagram of user interaction with a virtual display according to an embodiment.

FIG. 6 is a diagram of user interaction with a virtual display according to an embodiment. Input devices such as mouse or keyboards using the USB protocol follow a standard for communication (e.g., Human Interface Device) that can be emulated by a device that receives commands from an external system, e.g., a HMD 110. The visualization system 100 may provide device controls to an external device processor, e.g., of an input device, which may be used to control a virtual display.

In the embodiment shown in FIG. 6, the visualization system 100 determines that the user 105 wearing HMD 110 is looking at a virtual display 600. For instance, the visualization system 100 determines that the gaze direction of the user 105 intersects the plane of the display area of the virtual display 600. Alternatively, the visualization system 100 may determine that the virtual display 600 is within a field of view of the user (e.g., even if the user is not directly looking at the virtual display 600). The visualization system 100 may update the virtual display 600 to indicate to the user 105 that the virtual display 600 is selected for control. The visualization system 100 may provide device controls determined using gaze direction, other hands-free gestures of the user, or voice commands. The visualization system 100 may emulate function of a mouse by providing device controls to update position of a cursor 610 on the virtual display 600.

VII. Additional Considerations

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above disclosure.

Some portions of this description describe the embodiments of the invention in terms of algorithms and symbolic representations of operations on information. These algorithmic descriptions and representations are commonly used by those skilled in the data processing arts to convey the substance of their work effectively to others skilled in the art. These operations, while described functionally, computationally, or logically, are understood to be implemented by computer programs or equivalent electrical circuits, microcode, or the like. Furthermore, it has also proven convenient at times, to refer to these arrangements of operations as modules, without loss of generality. The described operations and their associated modules may be embodied in software, firmware, hardware, or any combinations thereof.

Any of the steps, operations, or processes described herein may be performed or implemented with one or more hardware or software modules, alone or in combination with other devices. In one embodiment, a software module is implemented with a computer program product including a computer-readable non-transitory medium containing computer program code, which can be executed by a computer processor for performing any or all of the steps, operations, or processes described.

Embodiments of the invention may also relate to a product that is produced by a computing process described herein. Such a product may include information resulting from a computing process, where the information is stored on a non-transitory, tangible computer readable storage medium and may include any embodiment of a computer program product or other data combination described herein.

As used herein any reference to "one embodiment" or "an embodiment" means that a particular element, feature, structure, or characteristic described in connection with the embodiment is included in at least one embodiment. The appearances of the phrase "in one embodiment" in various places in the specification are not necessarily all referring to the same embodiment.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Finally, the language used in the specification has been principally selected for readability and instructional purposes, and it may not have been selected to delineate or circumscribe the inventive subject matter. It is therefore intended that the scope of the invention be limited not by this detailed description, but rather by any claims that issue on an application based hereon. Accordingly, the disclosure of the embodiments of the invention is intended to be illustrative, but not limiting, of the scope of the invention, which is set forth in the following claims.

What is claimed is:

1. A method comprising:
receiving sensor data from a first head-mounted display (HMD) of a first user, wherein the first HMD displays a first virtual display to the first user;

determining, using the sensor data, one or more user inputs performed by the first user to interact with the first virtual display;
generating a graphical annotation using the one or more user inputs;
providing the graphical annotation for presentation by the first HMD as overlaid on the first virtual display to the first user;
determining that the first user is associated with the first virtual display;
determining that a second user is associated with a second virtual display displayed by a second HMD of the second user;
determining that the second virtual display is paired to the first virtual display at least by determining that the first user and the second user are participating in a same activity; and
providing the graphical annotation for presentation by the second HMD as overlaid on the second virtual display to the second user.

2. The method of claim 1, further comprising:
determining a gaze direction of the first user using orientation of a head of the first user and orientation of a pupil of the first user; and
determining that the gaze direction of the first user is directed toward the first virtual display.

3. The method of claim 2, further comprising:
determining a plane of the first virtual display; and
tracking movement of the gaze direction while the gaze direction intersects the plane of the first virtual display, wherein the graphical annotation is generated using the movement of the gaze direction.

4. The method of claim 3, further comprising:
responsive to determining that the gaze direction intersects the plane of the first virtual display, updating the first virtual display to indicate to the first user that the first virtual display is selected for control by the first user.

5. The method of claim 1, wherein the one or more user inputs do not require the first user to touch a physical input device, the method further comprising:
mapping each of the one or more user inputs to one of a plurality of device controls associated with the physical input device, wherein the graphical annotation is generated using the plurality of device controls.

6. The method of claim 1, wherein the one or more user inputs includes gaze direction, hand motion, and finger gesture.

7. The method of claim 1, further comprising:
determining that the one or more user inputs includes a voice command; and
determining a transcript of the voice command, wherein the graphical annotation is generated using the transcript.

8. The method of claim 1, further comprising:
determining that the second virtual display is paired to the first virtual display further by determining that the first user and the second user are located within a threshold distance from each other.

9. The method of claim 1, further comprising:
responsive to determining that the first virtual display has different dimensions than the second virtual display, performing one or more transformations to modify the graphical annotation presented to the second user.

10. A non-transitory computer-readable storage medium storing instructions, the instructions when executed by one or more processors cause the one or more processors to:
receive sensor data from a first head-mounted display (HMD) of a first user, wherein the first HMD displays a first virtual display to the first user;
determine, using the sensor data, one or more user inputs performed by the first user to interact with the first virtual display;
generate a graphical annotation using the one or more user inputs;
provide the graphical annotation for presentation by the first HMD as overlaid on the first virtual display to the first user;
determine that the first user is associated with the first virtual display;
determine that a second user is associated with a second virtual display displayed by a second HMD of the second user;
determine that the second virtual display is paired to the first virtual display at least by determining that the first user and the second user are participating in a same activity; and
provide the graphical annotation for presentation by the second HMD as overlaid on the second virtual display to the second user.

11. The non-transitory computer-readable storage medium of claim 10, storing further instructions that when executed by the one or more processors cause the one or more processors to:
determine a gaze direction of the first user using orientation of a head of the first user and orientation of a pupil of the first user; and
determine that the gaze direction of the first user is directed toward the first virtual display.

12. The non-transitory computer-readable storage medium of claim 11, storing further instructions that when executed by the one or more processors cause the one or more processors to:
determine a plane of the first virtual display; and
track movement of the gaze direction while the gaze direction intersects the plane of the first virtual display, wherein the graphical annotation is generated using the movement of the gaze direction.

13. The non-transitory computer-readable storage medium of claim 12, storing further instructions that when executed by the one or more processors cause the one or more processors to:
responsive to determining that the gaze direction intersects the plane of the first virtual display, update the first virtual display to indicate to the first user that the first virtual display is selected for control by the first user.

14. The non-transitory computer-readable storage medium of claim 10, storing further instructions that when executed by the one or more processors cause the one or more processors to:
map each of the one or more user inputs to one of a plurality of device controls associated with a physical input device, wherein the graphical annotation is generated using the plurality of device controls, and wherein the one or more user inputs do not require the first user to touch the physical input device.

15. The non-transitory computer-readable storage medium of claim 10, wherein the one or more user inputs includes gaze direction, hand motion, and finger gesture.

16. The non-transitory computer-readable storage medium of claim 10, storing further instructions that when executed by the one or more processors cause the one or more processors to:

determine that the one or more user inputs includes a voice command; and determine a transcript of the voice command, wherein the graphical annotation is generated using the transcript.

17. The non-transitory computer-readable storage medium of claim 10, storing further instructions that when executed by the one or more processors cause the one or more processors to:

determine that the second virtual display is paired to the first virtual display further by determining that the first user and the second user are located within a threshold distance from each other.

18. The non-transitory computer-readable storage medium of claim 10, storing further instructions that when executed by the one or more processors cause the one or more processors to:

responsive to determining that the first virtual display has different dimensions than the second virtual display, perform one or more transformations to modify the graphical annotation presented to the second user.

19. A system comprising:

a first head-mounted device (HMD) of a first user, wherein the first HMD displays a first virtual display to the first user;

a second HMD of a second user, wherein the second HMD displays a second virtual display to the second user; and a non-transitory computer-readable storage medium storing instructions, the instructions when executed by one or more processors cause the one or more processors to:

receive sensor data from the first HMD;

determine, using the sensor data, one or more user inputs performed by the first user to interact with the first virtual display;

generate a graphical annotation using the one or more user inputs;

provide the graphical annotation for presentation by the first HMD as overlaid on the first virtual display to the first user;

determine that the first user is associated with the first virtual display;

determine that the second user is associated with the second virtual display;

determine that the second virtual display is paired to the first virtual display at least by determining that the first user and the second user are participating in a same activity; and provide the graphical annotation for presentation by the second HMD as overlaid on the second virtual display to the second user.

20. The system of claim 19, wherein the non-transitory computer-readable storage medium stores further instructions that when executed by the one or more processors cause the one or more processors to:

determine a gaze direction of the first user using orientation of a head of the first user and orientation of a pupil of the first user; and track movement of the gaze direction while the gaze direction intersects a plane of the first virtual display, wherein the graphical annotation is generated using the movement of the gaze direction.

* * * * *